United States Patent
Womack et al.

(10) Patent No.: US 7,250,528 B2
(45) Date of Patent: Jul. 31, 2007

(54) PROCESS FOR PRODUCING INDENOL ESTERS OR ETHERS

(75) Inventors: Gary Bernard Womack, Hopewell, NJ (US); Roger Leslie Snowden, Viry (FR); Hervé Mosimann, Carouge (CH); Anthony Alexander Birkbeck, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 11/581,172

(22) Filed: Oct. 12, 2006

(65) Prior Publication Data

US 2007/0032402 A1 Feb. 8, 2007

Related U.S. Application Data

(63) Continuation of application No. PCT/IB2005/001474, filed on May 10, 2005, and a continuation-in-part of application No. 10/849,559, filed on May 18, 2004, now abandoned.

(51) Int. Cl.
*C07C 67/02* (2006.01)
*A61K 8/18* (2006.01)

(52) U.S. Cl. ............................ 560/255; 512/18; 512/19
(58) Field of Classification Search .................... None
See application file for complete search history.

(56) References Cited

OTHER PUBLICATIONS

Pincock, J. A. et al., XP009054483 "The Photochemistry Of Indenyl Alcohols And Esters: Substituent Effects On The Competition Between Ion- And Radical-Derived Products" Canadian Journal Of Chemistry, vol. 81 (10),pp. 1083-1095 (2003).
Kapur, S. et al. XP009054494, "Substituent Effects On The Rate Of Carbene Formation In The Pyrolysis Of Indenyl Diazo Compounds" Canadian Journal Of Chemistry, vol. 66 (11), 2888-93 (1988).
Abstract: accession No. rid 9727726, XP002355038.
Abstract: accession No. rid 2884274, XP002355039.
Abstract: accession No. rid 305299, XP002355040.
Abstract: accession No. rid 7987060, XP002355041.

*Primary Examiner*—Paul A. Zucker
(74) *Attorney, Agent, or Firm*—Winston & Strawn LLP

(57) ABSTRACT

The present invention relates to a process for making indenol esters or ethers from an α-substituted cinnamic aldehyde derivative such as an acetal or an acylal. Said reaction is promoted by the use of strong mineral acids, sulphonic acids, acidic zeolites or Lewis acids.

12 Claims, No Drawings

PROCESS FOR PRODUCING INDENOL ESTERS OR ETHERS

CROSS-REFERENCE TO RELATED APPLICATIONS

This application is a continuation of International application PCT/IB2005/001474 filed May 10, 2005, and a continuation-in-part of U.S. application Ser. No. 10/849,559 filed May 18, 2004, now abandoned the entire content of each of which is expressly incorporated herein by reference thereto.

TECHNICAL FIELD

The present invention relates to the field of organic synthesis. More particularly it provides a process for making an indenol ester or ether from an α-substituted cinnamic aldehyde derivative such as an acyclic acetal or an acylal. Said reaction is promoted by the use of strong mineral acids, sulphonic acids, acidic zeolites or Lewis acids.

BACKGROUND

The compounds of formula (I), as defined below, can be useful as perfuming ingredients and/or as starting material for the synthesis of compounds having a more complex skeleton.

The methods of preparation of said compounds reported in the prior art are in general quite long and/or expensive.

It is therefore highly desirable to access such compounds by means of a simple and efficient isomerisation process wherein the starting material is an easily accessible material. To the best of our knowledge, in the prior art there is no report of an isomerisation process giving a direct access to compounds of formula (I) from the compound of formula (II).

SUMMARY OF THE INVENTION

The present invention now relates to a process for making an indenol ester or ether wherein an α-substituted cinnamic acetal or acylal is treated with strong mineral protic acids, sulphonic acids, acidic zeolites and Lewis acids.

Furthermore, the invention also relates to specific compounds which can be obtained by the invention's process.

DETAILED DESCRIPTION OF THE PREFERRED EMBODIMENTS

In order to solve the problems aforementioned, a first embodiment of the present invention provides a process for making a compound of formula

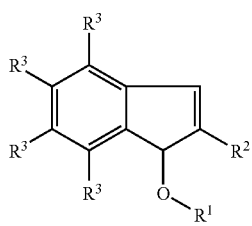

(I)

wherein $R^1$ represents a formyl group, a —COCOOH group or a group of formula —(CO)$_n$—R, n being 0 or 1 and R representing an optionally substituted phenyl group or a $C_{1-6}$ alkyl or alkenyl group optionally halogenated;

$R^2$ represents a $C_{1-10}$ alkyl or alkenyl group; and at least one $R^3$ represents a hydrogen atom and the other $R^3$ represent each a hydrogen atom or a $C_{1-5}$ alkyl, alkenyl or alkoxy group;

comprising the cyclisation, at a temperature above 10° C., of the corresponding compound of formula

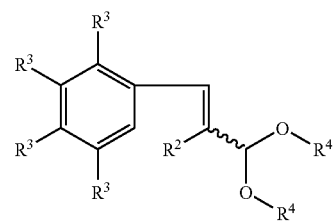

(II)

wherein each $R^4$, taken separately, represents a formyl group or a —(CO)$_n$—R group, or the $R^4$, taken together, represent a —COCO— group;

the wavy line indicates that the configuration of the carbon-carbon double bond is E or Z or a mixture thereof; and n, R, $R^2$, $R^3$ and $R^4$ have the meaning as indicated above;

in the presence of a compound, which promotes the reaction, selected from the group consisting of strong mineral protic acids, sulphonic acids, acidic zeolites and Lewis acids.

Examples of the substituent of R, when it is a phenyl, are one or two halogen atoms, $C_{1-5}$ alkyl or alkoxy or $CO_{0-6}$ amino groups. Examples of halogens for R are chlorine or fluorine atoms.

For the invention purpose, it is important that $R^2$ is not a hydrogen atom, indeed if $R^2$ is H then the reaction does not take place.

According to an embodiment of the present invention $R^1$ represents a group of formula —(CO)$_n$—R, n being 0 or 1 and R representing an optionally substituted phenyl group or a $C_{1-5}$ alkyl group.

According to another embodiment of the present invention, $R^2$ represents a $C_{1-6}$ alkyl group.

According to a further embodiment of the present invention, at least two $R^3$ represent a hydrogen atom and the other $R^3$ may represent each a hydrogen atom or a $C_{1-5}$ alkyl or alkoxy group.

According to a particular embodiment of the invention the compounds of formula (I) are of formula

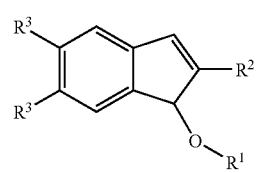

(I')

and are obtained by cyclisation of the corresponding compounds of formula

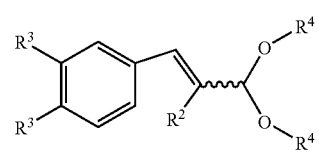

(II')

wherein the wavy line $R^1$, $R^2$ and $R^4$ have the same meaning as indicated above, and one $R^3$ is a hydrogen atom and the other $R^3$ is a $C_{1-5}$ alkyl group.

The compounds of formula (I') wherein one $R^3$ is a hydrogen atom and the other $R^3$ is a $C_{1-5}$ alkyl group are new compounds and can be used as starting compounds for the synthesis of indenols. Amongst said compounds of formula (I') can be cited the ones wherein $R^2$ is a methyl group and both $R^3$ are hydrogen atoms or the ones wherein $R^2$ is a methyl group and one $R^3$ is a hydrogen atom and the other $R^3$ is a methyl group.

Amongst the compounds of formula (I'), those of formula

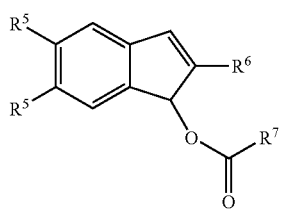

(III)

wherein one $R^5$ is a hydrogen atom and the other $R^5$ is a $C_{1-5}$ alkyl group and $R^6$ or $R^7$ represents a methyl or ethyl group; are also new and can be used as perfuming ingredient to impart floral and/or indole odor notes.

For example, one may cite 2,6-dimethyl-1H-inden-1-yl acetate which possesses an odor of the muguet, acetophenone type with some cedar and indol connotations, or also 2,6-dimethyl-1H-inden-1-yl propanoate which has a floral-estery odor.

The compounds, which can be used in the invention's process to promote it, are a strong mineral protic acid, a suphonic acid, an acidic zeolite or a Lewis acid. By "mineral" we mean here an acid having an anion which does not contain a carbon atom. By "strong" we mean here a protic acid having a $pK_{AB} < 3$, preferably below 2.

By "Lewis acid" we mean here an acid which is not essentially a protic acid. For example one may cite $BF_3$ and its adducts or Fe, Zn, Sn or Cd salts with weakly coordinating anions such as halides, sulphonates carboxylates or non-coordinating anion.

Said compounds can be in the anhydrous form or also in the hydrate form, except for those acids which are unstable in the presence of water.

According to another particular embodiment of the invention, the compound promoting the reaction is selected from the group consisting of $H_2SO_4$, p-toluenesulphonic acid, $NaHSO_4$, $KHSO_4$, $H_3PO_4$, HCl, $HNO_3$, $BF_3$ and its adducts with $C_{2-6}$ ethers or with $C_{2-6}$ carboxylic acids, poly(styrene sulphonic acid) based resins, K-10 Clay, $SnX_4$, $FeX_3$ and $ZnX_2$, $ZnI_2$, X representing a halogen atom, such as Cl or Br, or a $C_{1-6}$ carboxylate, such as acetate or trifluoroacetate, or a $C_{1-7}$ sulphonate, such as a triflate or tosylate.

Preferably, the catalyst is $H_3PO_4$, $FeX_3$ or $ZnX_2$, and in particular $FeCl_3$ or $ZnCl_2$.

Said compounds can be added to the reaction medium in catalytic or stoichiometric amounts or even in excess. As non-limiting examples, one can cite catalytic amounts ranging from 0.001 to 0.50 molar equivalents, relative to the molar amount of the starting compound (II). Preferably, the catalyst concentrations will be comprised between 0.005 and 0.30, or even between 0.005 and 0.15, molar equivalents. It goes without saying that the optimum concentration of catalyst will depend on the nature of the catalyst and on the desired reaction time.

Another parameter of the invention's process is the temperature. In order to allow the cyclisation to occur, it is useful to carry out the invention's process at a temperature of at least 10° C. Below said temperature the speed of the reaction decreases quite rapidly. The upper limit of temperature range is fixed by the reflux temperature of the reaction mixture that, as skilled persons know, depends on the exact nature of the starting and final product and optionally, as explained below, of the solvent. However, as non-limiting example, one can cite a preferred temperature ranging between 60° C. and 180° C. Of course, a person skilled in the art is also able to select the preferred temperature as a function of the melting and boiling point of the starting and final products as well as of the solvent.

The process of the invention can be carried out in the presence or in the absence of solvent. As a person skilled in the art can anticipate, the presence of a solvent is mandatory only in the case in which the starting compound is a solid compound under the reaction conditions.

However, according to a preferred embodiment of the invention, and independently of the physical state of the starting compound, the process is advantageously carried out in the presence of a solvent. Preferably, said solvent is anhydrous or does not contain more than 5% w/w water.

Non-limiting examples of such a solvent are $C_4$-$C_8$ ethers, $C_3$-$C_6$ esters, $C_3$-$C_6$ amides, $C_6$-$C_9$ aromatic solvents, $C_5$-$C_7$ linear or branched or cyclic hydrocarbons, $C_1$-$C_2$ chlorinated solvents and mixtures thereof.

Furthermore, the reaction can also be carried out in the presence of a solvent belonging to the family of orthoesters of formula $(RO)_3CR$ or, and preferably, to the family of carboxylic anhydride of formula $RC(O)O(O)CR$, R being defined as above, optionally containing the corresponding carboxylic acid $R^8COOH$.

The compound of formula (II) can be made and isolated according to any prior art method. Alternatively, compound (II) can be also generated in situ, i.e. in the reaction medium just before its use, according to any know prior art method.

In particular, preferably the compound of formula (II) is made or generated by a method using the corresponding enal as starting material. Indeed, the enal can be easily obtained by an aldol condensation, as a person skilled in the art knows well.

Therefore, another object of the present invention is an invention's process, as defined above, further comprising the step of generating in situ the compound of formula (II) starting from the corresponding enal of formula (IV)

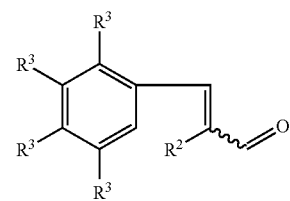

wherein $R^2$ and $R^3$ have the same meaning indicated above.

A process comprising the in situ generation of the compound of formula (II) is particularly useful when said compound (II) is an acylal, i.e. a geminal dicarboxylate.

Now, when the compound of formula (II) is an acylal, we have also noticed that the compounds that are able to promote the cyclisation of the acylal are also useful to promote the conversion of the enal into the corresponding acylal.

Therefore, another object of the present invention, and in fact a particular embodiment of the above-mentioned process, is a process for making an ester of formula (I), as defined above, comprising the step of reacting, in the presence of a catalyst as defined for the cyclisation step, an enal of formula (IV), as defined above, with an orthoesters of formula $(RO)_3CR$ or, and preferably, a carboxylic anhydride of formula $RC(O)O(O)CR$, R being defined as above.

EXAMPLES

The invention will now be described in further detail by way of the following examples, wherein the abbreviations have the usual meaning in the art, the temperatures are indicated in degrees centigrade (° C.). The NMR spectral data were recorded in $CDCl_3$ at 400 MHz or 100 MHz for $^1H$ or $^{13}C$, respectively, the chemical displacements δ are indicated in ppm with respect to TMS as standard, and the coupling constants J are expressed in Hz. All the abbreviations have the usual meaning in the art.

Example 1

Cyclisation of 2-alkylcinnamic Aldehyde via the Acylal Derivative a) Preparation of 2-pentyl-1H-inden-1-yl Acetate 4.13 ml of a 0.25 M solution of $FeCl_3.6H_2O$ in $Ac_2O$ (1.03 mmol) where diluted into $Ac_2O$ (30.2 g) and the resulting solution was added dropwise during 1 hour to a stirred solution of 2-pentylcinnamaldehyde (20 g, 99 mmol) in AcOH (18.5 g) at reflux.

After a further 2 hours at reflux the cooled mixture was poured into a mixture of $H_2O$ and $Et_2O$. Then, solid $Na_2CO_3$ (44.7 g) was added portionwise to the stirred mixture. After one hour stirring the aqueous phase was saturated with NaCl and extracted with $Et_2O$. The organic layers were dried over anhydrous $Na_2SO_4$, and the solvent evaporated to afford a crude product, which was further purified by distillation under vacuum to give the desired compound (yield=87%).

B.p. 86-93°/0.05 mbar. $^1H$-NMR: 0.90 (br.t, J=7, 3H); 1.35 (4H); 1.58 (m, 2H); 2.17 (s, 3H); 2.29 (m, 2H); 6.21 (s, 1H); 6.43 (s, 1H); 7.09 (dd, J=7, J=7, 1H); 7.13 (d, J=7, 1H); 7.23(m, 1H); 7.37 (d, J=7, 1H). $^{13}C$-NMR: 171.4 (s); 149.2 (s); 143.7 (s); 142.0 (s); 128.9 (d); 128.2 (d); 125.1 (d); 124.2 (d); 120.4 (d); 77.5 (d); 31.7 (t); 28.2 (t); 27.7 (t); 22.5 (t); 21.1 (q); 14.0 (q b) Preparation of 2-hexyl-1H-inden-1-yl Acetate Using the same experimental procedure as under a), 2-hexylcinnamaldehyde (20 g, 92.6 mmol), $FeCl_3.6H_{22}O$ (3.85 ml of a 0.25 M solution in $Ac_2O$, 0.96 mmol), $Ac_2O$ (28.3 g, 0.28 mol) in AcOH (17.4 g) were reacted together. After a further 3 hours at reflux the cooled mixture was treated to the same workup as before to provide the title compound (yield=83%). B.p. 89-101°/0.035 mbar. $^1H$-NMR: 0.89 (t, J=7,3 H); 1.25-1.40 (6H); 1.58 (m, 2H); 2.17 (s, 3H); 2.29(m, 2H); 6.21 (s, 1H); 6.43 (s, 1H); 7.09 (dd, J=7, J=7, 1H); 7.13 (d, J=7, 1H); 7,22(m, 1H); 7.36 (d, J=7, 1H). $^{13}C$-NMR: 171.4 (s); 149.3 (s); 143.7 (s); 142.0 (s); 128.9 (d); 128.2 (d); 125.1 (d); 124.2 (d); 120.4 (d); 77.5 (d); 31.7 (t); 29.1 (t); 28.3 (t); 28.0 (t); 22.6 (t); 21.1 (q 14.1 (q).

c) Preparation of 2-methyl-1H-inden-1-yl Acetate

Using the same experimental procedure as under a), 2-methylcinnamaldehyde (21 g, 0.14 mol) in AcOH (27 g), $FeCl_3·6H_2O$ (6 ml of a 0.25 M solution in $Ac_2O$, 1.5 mmol) in $Ac_2O$ (53 g) were reacted together. After a further 2 hours at reflux the cooled mixture was treated to the same workup and purification as before to provide the title compound (yield=70%). B.p. 70-95°/0.04 mbar. $^1H$-NMR: 1.98 (s, 3H); 2.18 (s,3H); 6.15 (s, 1H); 6.41 (s,1H); 7.09 (dd, J=7, 7, 1H); 7.12 (d, J=7, 1H); 7.23 (m,1H); 7.37 (d, J=7, 1H). $^{13}C$-NMR: 171.5 (s); 144.4 (s); 143.7 (s); 142.1 (s); 129.3 (d); 128.9 (d); 125.1 (d); 124.2 (d); 120.3 (d); 78.4 (d); 21.1 (q); 14.0 (q).

Example 2 a) Preparation of 1-methoxy-2-methyl-1H-indene via Cyclisation of the Acetal

A solution of $FeCl_3$ anhydrous (42 mg, 0.25 mmol) in BuOAc (4 ml) was added dropwise during 10 minutes to a stirred solution of the 3,3-dimethoxy-2-methyl-1-phenyl-1-propene (5 g, 24.7 mmol) in BuOAc (13 ml) at 123° C. After 3 hours the cooled mixture was diluted with $Et_2O$ (50 ml) and washed with saturated aqueous $NaHCO_3$ and brine. Extraction, drying over anhydrous $Na_2SO_4$, concentration and fractional distillation under vacuum gave a crude product that was further purified by chromatography ($SiO_2$, cyclohexane/AcOEt 95:5 then AcOEt/$Et_2O$ 1:1). There was thus obtained the title compound with a yield of 33%.

B.p. 32-43°/0.07 mbar. $^1H$-NMR: 2.03 (s, 3H); 3.03 (s, 3H); 4.85 (s,1H); 6.44 (s, 1H); 7.09 (dd, J=7, J=7, 1H); 7.11 (d, J=7, 1H); 7,22 (m, 1H); 7.41 (d, J=7, 1H). $^{13}C$-NMR: 145.9 (s); 143.9 (s); 141.8 (s); 128.7 (d); 128.4 (d); 124.6 (d); 123.7 (d); 120.1 (d); 84.9 (d); 51.8 (q); 14.1 (q).

b) Preparation of 2-methyl-1H-inden-1-yl Acetate via Cyclisation of the Acylal

A solution of $FeCl_3$ anhydrous (21 mg, 0.125 mmol) in BuOAc (2 ml) was added dropwise during 5 minutes to a stirred solution of the 2-methyl-3-phenyl-2-propenylidene diacetate (3.1 g, 12.5 mmol) in BuOAc (8 ml) at 123°. After 2 h at 123° the reaction was stopped and worked-up as above. Chromatography ($SiO_2$, cyclohex/AcOEt 9:1) of the crude product allowed the isolation of the title acetate (62% yield). Identical spectra as previously described.

Example 3

Synthesis of 2,6-dimethyl-1H-inden-1-yl Acetate from the Corresponding Aldehyde

A solution of (2E)-2-methyl-3-(4-methylphenyl)-2-propenal (100.0 g, 0.62 mol) in cyclohexane (300.0 g) was added dropwise in 2 hours to a stirred solution of zinc chloride (3.1 g, 22 mmol) in acetic anhydride (188.4 g, 1.85 mol) at 80° C. The reaction mixture was stirred further at 80° C. for 18 hours and then cooled to 25° C. The mixture was washed twice with water (100.0 g) and a 5% aqueous solution of sodium carbonate (100.0 g) and concentrated under reduced pressure. The crude product was flash-distilled (B.p.: 75-90° C./0.1 mbar) affording 88.5 g of the desired acetate (69%) as a yellow liquid (purity: 97.1% GC).

1H-NMR: 7.19 (s, 1H); 7.03 (d, J=7.9, 1H); 6.99 (d, J=7.9, 1H); 6.37 (s, 1H); 6.11 (s, 1H); 2.31 (s, 3H); 2.17 (s, 3H); 1.95 (s, 3H). $^{13}C$-NMR: 171.5 (s); 143.3 (s); 142.3 (s); 141.0 (s); 134.8 (s); 129.2 (d); 125.2 (d); 120.0 (d); 78.4 (d); 21.3 (q); 21.1 (q); 14.0 (q).

Example 4

Synthesis of 2.6-dimethyl-1H-inden-1-yl Acetate from the Corresponding Aldehyde

General Procedure

A solution of (2E)-2-methyl-3-(4-methylphenyl)-2-propenal (100.0 g, 0.62 mol) in acetic anhydride (100.0 g) was added dropwise in 2 hours to a stirred solution of the catalyst in acetic anhydride (88.4 g, 1.85 mol in total) at 80° C. The reaction mixture was stirred further at 80° C. until the complete conversion of the starting material and then cooled to 25° C. The mixture was diluted with methyl tert-butyl ether (300.0 g), washed successively with water (twice 100.0 g) and a 5% aqueous solution of sodium carbonate (100.0 g) and concentrated under reduced pressure. The crude product was flash-distilled (B.p.: 75-90° C./0.1 mbar) affording the desired acetate as a yellow liquid.

The results obtained are listed in the following table:

| Catalyst | Reaction time | Isolated yield |
|---|---|---|
| $H_3PO_4$ (0.072 eq.) | 22 h. | 51% |
| $BF_3 \cdot OEt_2$ (0.036 eq.) | 19 h. | 37% |
| $ZnBr_2$ (0.036 eq.) | 5 h. | 55% | eq. = molar equivalents in respect to the starting material
h = hours

Example 5

Synthesis of 1-ethoxy-2-butyl-1H-indene from the Corresponding Aldehyde

A mixture of 2-butylcinnamic aldehyde (5 g, 26.7 mmol.), triethyl orthoformate (5.9 g, 40 mmol.), absolute ethanol (10 g, 217 mmol.) and AMBERLYST® 15 catalyst (0.52 g) was heated at reflux (85° C. oil bath). After three days, the mixture was filtered and concentrated under vacuum. The residue was subjected to silica gel flash chromatography (hexane/ethyl acetate 98:2), yielding 3.8 g (17.6 mmol., 66% yield) of the indenyl ethyl ether.

$^1$H-NMR: 0.95 (t, J=7.4, 3H), 1.15 (t, J=6.9, 3H), 1.46-1.36 (m, 2H), 1.70-1. 2.30 (m, 2H), 3.27-3.15 (m, 2H), 4.95 (s, 1H), 6.41 (s, 1H), 7.1 (t, J=7.2, 1(d, J=7.2, 1H), 7.21 (t, J=7.2, 1H), 7.42 (d, J=7.2, 1H). $^{13}$C-NMR: 14.0 (q), 15.7 (q), 22.7 (t), 28.1 (t), 30.5 (t), 60.0 (t), 83.4 (d), 120.2 (d) 124.6 (d), 126.9 (d), 128.3 (d), 142.5 (s), 143.6 (s), 151.3 (s).

Example 6

Synthesis of 2-ethyl-1H-inden-1-yl Acetate

A mixture of (E)-2-ethylcinnamaldehyde (8 g, 50 mmol.) and acetic anhydride (7.7 g, 75 mmol.) was cooled in an ice bath. Anhydrous $FeCl_3$ (0.3 g, 1.8 mmol.) was added and the mixture stirred for 15 minutes. The reaction mixture was removed from the cold bath and stirred at room temperature for one day. It then was diluted with 100 ml of diethyl ether and washed with water (2×50 ml). The organic phase was dried ($MgSO_4$), filtered and concentrated. Kugelrohr distillation (95-105° C., 24 mTorr) yielded 8.0 g (39.6 mmol., 79% yield) of the title compound.

IR (film) $v_{co}$ 1738 cm$^{-1}$. $^1$H-NMR: 1.19 (t, J=7.4 Hz, 3H); 2.16 (s, 3H); 2.32 (m, 2H); 6.22 (s, 1H); 6.43 (s, 1H); 7.08 (t, J=7 Hz, 1H); 7.13 (d, J=7 Hz, 1H); 7.22 (t, J=7 Hz, 1H); 7.36 (d, J=7 Hz, 1H). $^{13}$C-NMR: 12.3 (q); 21.1 (q); 21.5 (t); 77.6 (d); 120.5 (d); 124.2 (d); 125.1 (d); 127.4 (d); 128.9 (d); 142.0 (s); 143.6 (s); 150.7 (s); 171.5 (s).

Example 7

Synthesis of 2-isopropyl-1H-inden-1-yl Acetate

A mixture of (E)-2-isopropylcinnamaldehyde (18 g, 103 mmol.) and acetic anhydride (15.9 g, 155 mmol.) was cooled in an ice bath. Anhydrous $FeCl_3$ (0.75 g, 4.6 mmol.) was added and the mixture stirred for 15 minutes. The reaction mixture was removed from the cold bath and stirred at room temperature for one day. It then was diluted with 100 ml of diethyl ether and washed with water (2×100 ml). The organic phase was dried ($MgSO_4$), filtered and concentrated. Kugelrohr distillation (93-104° C., 30 mTorr) yielded 18.2 g (84 mmol., 82% yield) of the title compound.

IR (film) $v_{co}$ 1739 cm$^{-1}$. $^1$H-NMR: 1.15 (d, J=6.7 Hz, 3H); 1.23 (d, J=6.7 Hz, 3H); 2.17 (s, 3H); 2.59 (sp, J=6.7 Hz, 1H); 6.34 (s, 1H); 6.44 (s, 1H); 7.09 (t, J=7 Hz, 1H); 7.14 (d, J=7 Hz, 1H); 7.23 (t, J=7 Hz, 1H); 7.35 (d, J=7 Hz, 1H). $^{13}$C-NMR: 20.9 (q); 21.1 (q); 22.9 (q); 27.3 (d); 76.6 (d); 120.6 (d); 124.2 (d); 125.2 (d); 126.6 (d); 128.9 (d); 142.1 (s); 143.4 (s); 155.0 (s); 171.4 (s).

Example 8

Synthesis of 1-ethoxy-2,6-dimethyl-1H-indene

Anhydrous $FeCl_3$ (2.0 g, 12.3 mmol.) was added to a solution of (2E)-2-methyl-3-(4-methylphenyl-2-propenal (5.0 g, 31.3 mmol.) and triethyl orthoformate (5.1 g, 34.5 mmol.) in dichloromethane (35 ml). The dark red solution was stirred at room temperature for 1 day, then diluted with 100 ml of diethyl ether and washed with water (3×75 ml). The organic phase was dried ($MgSO_4$), filtered and concentrated. Kugelrohr distillation (54° C., 20 mTorr) yielded 1.4 g (7.4 mmol., 24% yield) of the title compound.

$^1$H-NMR: 1.66 (t, J=7, 3H); 2.01 (s, 3H); 2.34 (s, 3H); 3.22 (m, 2H); 4.84 (s, 1H); 7.0 (m, 2H); 7.24 (s, 1H). $^{13}$C-NMR: 14.1 (q); 15.7 (q); 21.4 (q); 59.9 (t); 84.4 (d); 119.7 (d); 124.7 (d); 128.0 (d); 128.7 (d); 134.2 (s); 141.0 (s); 142.9 (s); 145.3 (s).

Example 9

Synthesis of 1-methoxy-2,6-dimethyl-1H-indene

Anhydrous $FeCl_3$ (2.0 g, 12.3 mmol.) was added to a solution of (2E)-2-methyl-3-(4-methylphenyl) -2-propenal (5.0 g, 31.3 mmol.) and trimethyl orthoformate (36.4 g, 34.3 mmol.) in dichloromethane (35 ml). The dark red solution was stirred for one hour, then diluted with 100 ml of diethyl ether and washed with water (3×75 ml). The organic phase was dried ($MgSO_4$), filtered and concentrated. Kugelrohr distillation (65-80° C., 20 mTorr) yielded 3.2 g (18.4 mmol., 59% yield) of the title compound.

$^1$H-NMR: 2.00 (s, 3H); 2.35 (s, 3H); 3.03 (s, 3H); 4.82 (s, 1H); 6.40 (s, 1H); 7.02 (m, 2H); 7.24 (s, 1H). $^{13}$C-NMR: 14.1 (q); 21.4 (q); 51.8 (q); 84.8 (d); 119.8 (d); 124.8 (d); 128.5 (d); 128.8 (d); 134.3 (s); 141.2 (s); 142.1 (s); 144.7 (s).

Example 10

Synthesis of 2,6-dimethyl-1H-inden-1-yl Propionate from the Corresponding Aldehyde Same procedure as for the corresponding acetate (example 3) but using propionic anhydride instead of acetic anhydride. The crude product was distilled through a short Vigreux column (B.p.: 75-90° C. /0.1 mbar) affording 98.0 g of the desired propionate (71%) as a yellow liquid (purity: 97.3% GC).

$^1$H-NMR: 7.18 (s, 1H); 7.02 (d, J=8.2, 1H); 6.99 (d, J=8.2, 1H); 6.38 (s, 1H); 6.13 (s, 1H); 2.45 (q, J=7.7, 2H); 2.31 (s, 3H); 1.95 (s, 3H); 1.22 (t, J=7.7, 3H).

$^{13}$C-NMR: 175.0 (s); 143.4 (s); 142.5 (s); 141.0 (s); 134.8 (s); 129.2 (d); 129.1 (d); 125.2 (d); 120.0 (d); 78.3 (d); 27.8 (1); 21.3 (q); 14.0 (q); 9.3 (q).

What is claimed is:

1. A process for making a compound of formula

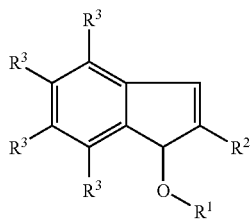
(I)

wherein $R^1$ represents a formyl group, a —COCOOH group or a group of formula —(CO)$_n$—R, n being 0 or 1 and R representing an optionally substituted phenyl group or a $C_{1-6}$ alkyl or alkenyl group optionally halogenated;

$R^2$ represents a $C_{1-10}$ alkyl or alkenyl group; and at least one $R^3$ represents a hydrogen atom and the other $R^3$ represent each a hydrogen atom or a $C_{1-5}$ alkyl, alkenyl or alkoxy group;

comprising the cyclisation, at a temperature above 10° C., of the corresponding compound of formula

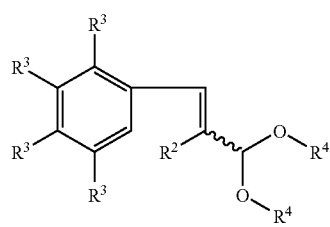
(II)

wherein each $R^4$, taken separately, represents a formyl group or a —(CO)$_n$—R group, or the $R^4$, taken together, represent a —COCO— group;

the wavy line indicates that the configuration of the carbon-carbon double bond is E or Z or a mixture thereof; and n, R, $R^2$, $R^3$ and $R^4$ have the meaning as indicated above;

in the presence of a compound, which promotes the reaction, selected from the group consisting of strong mineral protic acids, sulphonic acids, acidic zeolites and Lewis acids.

2. A process according to claim 1, wherein $R^1$ represents a group of formula —(CO)$_n$—R, n being 0 or 1 and R representing an optionally substituted phenyl group or a $C_{1-5}$ alkyl group and $R^2$ represents a $C_{1-6}$ alkyl group.

3. A process according to claim 1, wherein the compounds of formula (I) are of formula

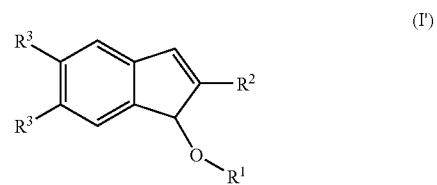
(I')

and are obtained by cyclisation of the corresponding compounds of formula

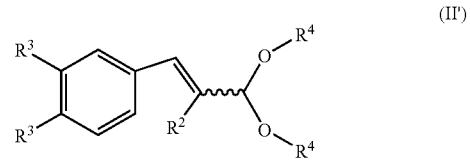
(II')

wherein the wavy line $R^1$, $R^2$, $R^3$ and $R^4$ have the same meaning as in claim 1.

4. A process according to claim 1, wherein the compound, which promotes the reaction, is selected from the group consisting of $H_2SO_4$, p-toluenesulphonic acid, NaHSO$_4$, KHSO$_4$, $H_3PO_4$, HCl, HNO$_3$, BF$_3$ and its adducts with $C_{2-6}$ ethers or with $C_{2-6}$ carboxylic acids, poly(styrene sulphonic acid) based resins, K-10 Clay, SnX$_4$, FeX$_3$ and ZnX$_2$, ZnI$_2$, X representing a halogen atom, such as Cl or Br, or a $C_{1-6}$ carboxylate, such as acetate or trifluoroacetate, or a $C_{1-7}$ sulphonate, such as a triflate or tosylate.

5. A process according to claim 4, wherein the compound is $H_3PO_4$, FeX$_3$ or ZnX$_2$, X having the same meaning as in claim 4.

6. A process according to claim 1, wherein said process is carried out in the presence of a carboxylic anhydride of formula RC(O)O(O)CR or of a orthoester of formula (RO)$_3$CR, R being as defined in claim 1.

7. A process according to claim 1, wherein said process further comprises the step of generating in situ the compound of formula (II) starting from the corresponding enal of formula

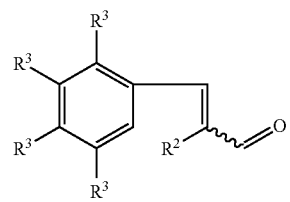
(IV)

wherein $R^2$ and $R^3$ have the same meaning as indicated in claim 1.

8. A compound of formula

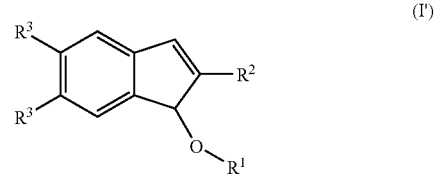
(I')

wherein one $R^3$ is a hydrogen atom and the other $R^3$ is a $C_{1-5}$ alkyl group, and $R^1$ and $R^2$ have the same meaning as in claim 1.

9. A compound according to claim 8, wherein $R^2$ is a methyl group and both $R^3$ are hydrogen atoms or $R^2$ is a methyl group and one $R^3$ is a hydrogen atom and the other $R^3$ is a methyl group.

10. A compound of formula

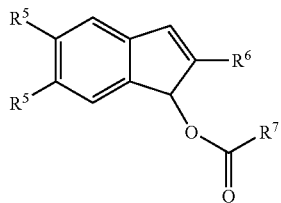

(III)

wherein one $R^5$ is a hydrogen atom and the other $R^5$ is a $C_{1-5}$ alkyl group and $R^6$ or $R^7$ represents a methyl or ethyl group.

11. A compound according to claim 10, wherein said compound is 2,6-dimethyl-1H-inden-1-yl acetate or 2,6-dimethyl-1H-inden-1-yl propanoate.

12. A method to confer, enhance, improve or modify the odor properties of a perfuming composition or of a perfumed article, which method comprises adding to said composition or article an effective amount of at least a compound according to claim 10 as perfuming ingredient.

* * * * *

UNITED STATES PATENT AND TRADEMARK OFFICE
CERTIFICATE OF CORRECTION

| | |
|---|---|
| PATENT NO. | : 7,250,528 B2 |
| APPLICATION NO. | : 11/581172 |
| DATED | : July 31, 2007 |
| INVENTOR(S) | : Womack et al. |

Page 1 of 1

It is certified that error appears in the above-identified patent and that said Letters Patent is hereby corrected as shown below:

<u>Column 10</u>:
Line 29 (claim 4, line 6), after "acid) based resins, K-10 Clay, $SnX_4$, $FeX_3$ and $ZnX_2$," change "$Zn1_2$," to -- $ZnI_2$, --.

Signed and Sealed this

Eighteenth Day of September, 2007

JON W. DUDAS
*Director of the United States Patent and Trademark Office*